US007556772B2

(12) United States Patent
Horan et al.

(10) Patent No.: US 7,556,772 B2
(45) Date of Patent: *Jul. 7, 2009

(54) LIQUID ANALYSER

(75) Inventors: Martin Horan, County Cork (IE);
Seamus O'Mahony, County Cork (IE)

(73) Assignee: Analytical Developments Limited, County Cork (IE)

( * ) Notice: Subject to any disclaimer, the term of this patent is extended or adjusted under 35 U.S.C. 154(b) by 629 days.

This patent is subject to a terminal disclaimer.

(21) Appl. No.: 11/235,176

(22) Filed: Sep. 27, 2005

(65) Prior Publication Data

US 2006/0073605 A1   Apr. 6, 2006

(30) Foreign Application Priority Data

Sep. 27, 2004 (IE) ............................... S2004/0655

(51) Int. Cl.
 *B01J 19/00* (2006.01)
 *G01N 35/00* (2006.01)
(52) U.S. Cl. ..................... 422/78; 422/68.1; 422/82.08; 422/82.09; 436/172
(58) Field of Classification Search ................ 422/68.1, 422/78, 82.05–82.09, 82.11, 236, 237; 436/145, 436/146, 160, 164–166, 172
See application file for complete search history.

(56) References Cited

U.S. PATENT DOCUMENTS

| 5,270,216 | A | * | 12/1993 | Kan et al. .................... 436/103 |
| 5,324,666 | A | * | 6/1994 | Siepmann et al. .............. 436/62 |
| 5,733,789 | A | * | 3/1998 | Wright et al. ................ 436/146 |
| 6,177,276 | B1 | * | 1/2001 | Richardson et al. ........... 436/55 |
| 6,623,974 | B1 | | 9/2003 | Horan et al. |

FOREIGN PATENT DOCUMENTS

EP   1 039 294 A2   9/2000
WO   WO-94/07134 A   3/1994

* cited by examiner

*Primary Examiner*—Jill Warden
*Assistant Examiner*—Shogo Sasaki
(74) *Attorney, Agent, or Firm*—Buskop Law Group, P.C.; Wendy Buskop

(57) ABSTRACT

A liquid analyser has a reactor portion and an associated measurement portion. A sample pump is operable to deliver a liquid sample to a reactor vessel. A base pump supplys a base solution to the reactor vessel. An ozone generator supplies ozone to the reactor vessel. The liquid sample is oxidised in the reactor vessel by means of hydroxyl radicals which are generated using the base solution and ozone to reduce complex components of the liquid sample to their lowest state in solution. The oxidised sample solution is delivered to an optical detector in the measurement portion to determine the concentration of one or more selected materials such as nitrogen, phosphorous or a heavy metal in the oxidised sample solution.

5 Claims, 7 Drawing Sheets

LIQUID ANALYSER

BACKGROUND OF THE INVENTION

This invention relates to a system for the analysis of one or more selected components in a liquid, and particularly in aqueous solutions.

SUMMARY OF THE INVENTION

According to the invention, there is provided an analytical method for measuring the quantity of one or more selected components in a liquid sample, including:
  taking a liquid sample;
  oxidising the liquid sample by means of hydroxyl radicals which are generated using a base solution and ozone for reducing complex components of the liquid sample to their lowest state in solution; and
  measuring the concentration of one or more selected materials in the oxidised liquid sample solution.

In one embodiment the method includes:
  delivering the liquid sample to a reactor vessel;
  adding a base liquid having hydroxyl ions to the liquid sample;
  adding ozone to the liquid sample and mixing the solution to form hydroxyl radicals which attack chemical bonds and reduce them to their lowest state;
  cutting off the ozone; and
  delivering oxidised sample liquid from the reactor vessel to a detector which is operable for determining the concentration of one or more selected materials in the oxidised sample liquid.

In another embodiment the method includes adding acid to the sample liquid in the reactor vessel and sparging to remove carbonate.

In a further embodiment the method includes adding a catalyst to the sample liquid for reducing oxalate to carbonate.

In another embodiment the catalyst is a metallic catalyst.

In another embodiment the catalyst is manganese.

In another embodiment the detector is an optical detector.

In another embodiment the method includes mixing the sample liquid with an associated reagent to form a coloured complex prior to delivering the coloured complex to the optical detector and measuring the coloured complex in the optical detector to give an indication of the content of the selected material or materials present in the sample liquid.

In another embodiment the selected material is a nitrogen compound.

In another embodiment the selected material is a phosphorous compound.

In another embodiment the selected materials are both a nitrogen compound and a phosphorous compound.

In another embodiment the selected material is ammonia.

In another the selected material is a heavy metal.

In another embodiment the selected material is chosen from the group including iron, copper, aluminium, cobalt, magnesium, and nickel.

In another embodiment the optical detector includes a light source together with at least one diode for optical measurement and a measurement cell through which light is directed from the light source for detection by the diode.

In another embodiment a photodiode array is provided in the optical detector for optical measurement of the liquid samples.

In another embodiment the method includes cleaning and flushing the detector between measuring different liquid samples.

In another embodiment the ozone is cut off either before or after adding the acid.

In another embodiment the ozone is cut off during the addition of the acid.

In another embodiment some ozone is added to the liquid sample prior to adding base solution to the liquid sample.

In another embodiment the method includes the step of stripping carbon dioxide from the reactor vessel and delivering the carbon dioxide through a carbon dioxide analyser for determining a value for carbon present in the liquid sample.

In another aspect the invention provides a liquid analyser, including:
  a reactor vessel;
  an ozone generator having an ozone outlet connected to the reactor vessel to deliver ozone to the reactor vessel;
  a sample pump having an inlet for connection to a source of a liquid to be tested, and an outlet connected to the reactor vessel;
  a base pump having an inlet for connection to a base solution reservoir and an outlet connected to the reactor vessel;
  the reactor vessel having an outlet for discharge of oxidised liquid sample from the reactor vessel;
  means for delivering oxidised liquid sample from said outlet to a detector, said detector been operable to measure the concentration of one or more selected materials in the oxidised liquid sample.

In another embodiment said delivering means includes a sample chamber connected to the outlet of the reactor vessel for reception of oxidised liquid sample from the reactor vessel, an analysis pump having an inlet connected to the sample chamber and an outlet connected to the detector.

In another embodiment means is provided for delivering a cleaning fluid to the detector for cleaning the detector.

In another embodiment means is provided for delivering a flushing fluid to the detector.

In another embodiment the detector is an optical detector.

In another embodiment means is provided for mixing a reagent with the oxidised sample liquid upstream of the detector.

In another embodiment said means is a reagent pump having an inlet connected to a reagent reservoir and an outlet connected to an inlet of a mixer, the outlet of the analysis pump also being connected to the mixer inlet, an outlet of the mixer being connected to the detector.

In another embodiment an acid pump is provided having an inlet for connection to an acid reservoir and an outlet connected to the reactor vessel.

In another embodiment means is provided for cleaning a sample delivery line communicating between the sample pump and the reactor vessel.

BRIEF DESCRIPTION OF THE DRAWINGS

The invention will be more clearly understood by the following description of some embodiments thereof, given by way of example only, with reference to the accompanying drawings, in which.

DETAILED DESCRIPTION OF PREFERRED EMBODIMENTS

Figure 1:
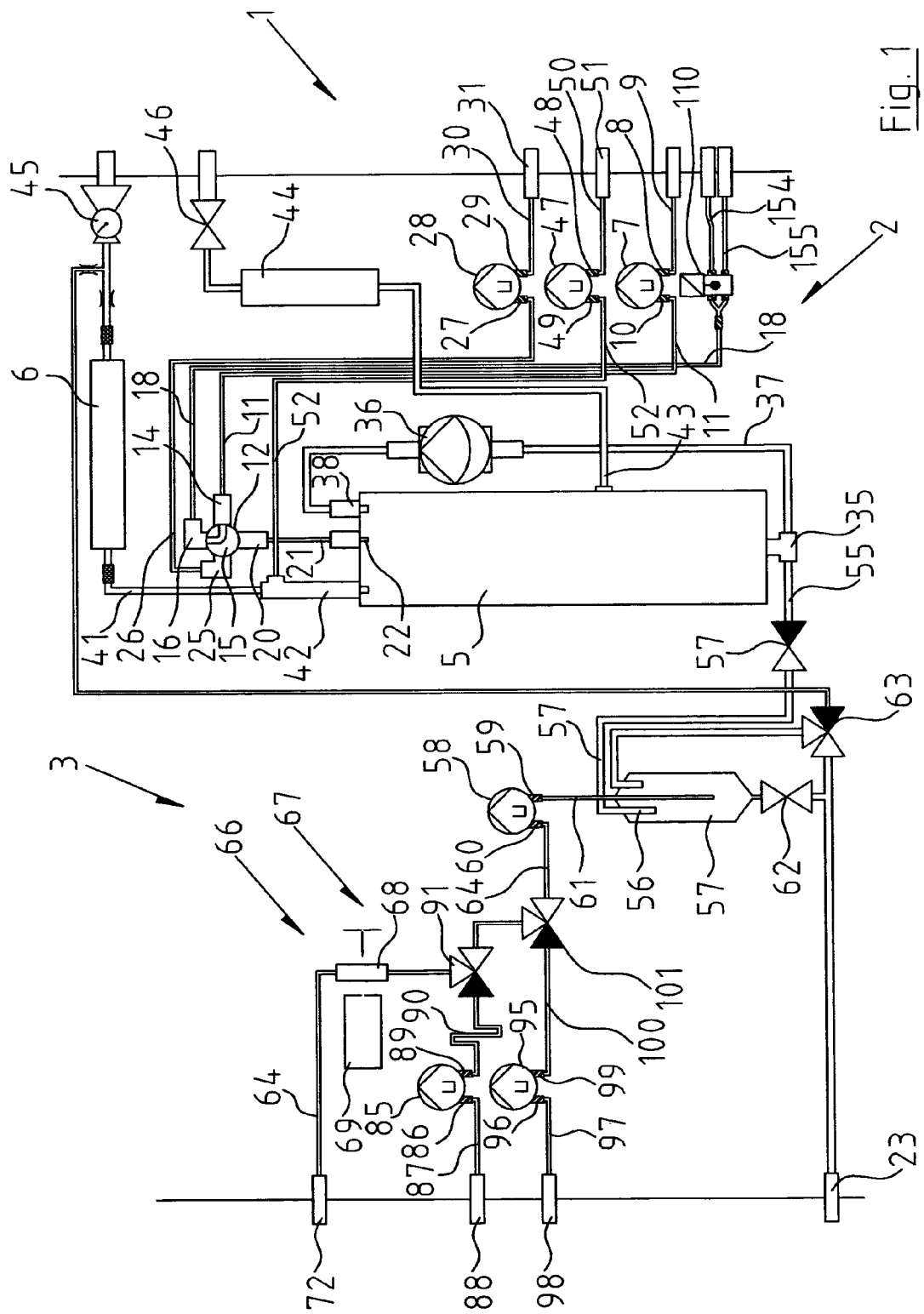
FIG. 1 is a schematic illustration of a liquid analyser according to the invention.

Referring to the drawings and initially to FIG. 1 thereof, there is illustrated a liquid analyser according to the invention indicated generally by the reference numeral 1. The liquid analyser 1 comprises a reactor portion indicated generally by the reference numeral 2 and an associated measurement portion indicated generally by the reference numeral 3. In this case the measurement portion 3 is adapted for measurement of the total nitrogen content of a sampled liquid.

A sample pump 7 has an inlet 8 connected by an inlet line 9 to the liquid to be tested. An outlet 10 of the sample pump 7 is connected by a sample delivery line 11 to a sampling valve 12 for delivery of a liquid sample to a first sample inlet 14 of the sampling valve 12.

Figure 6A:
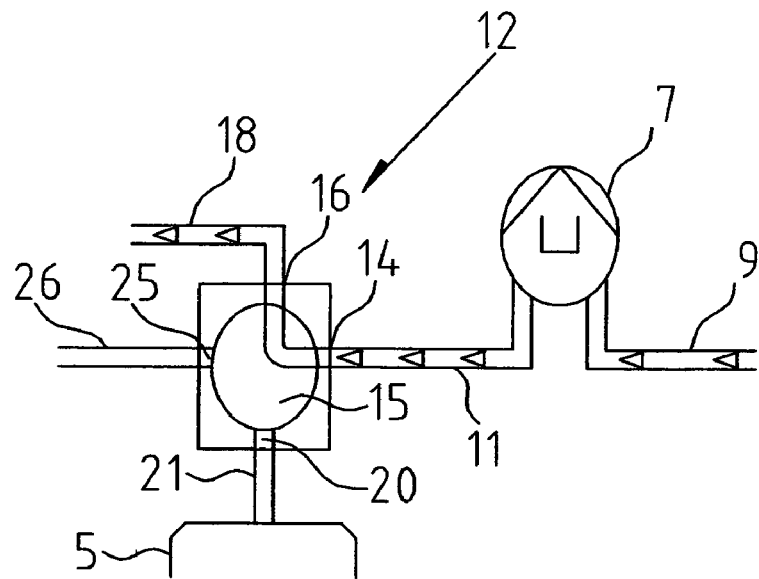
FIG. 6 has schematic illustrations showing a sampling valve portion of the analysers in different modes of operation.
Figure 6B:
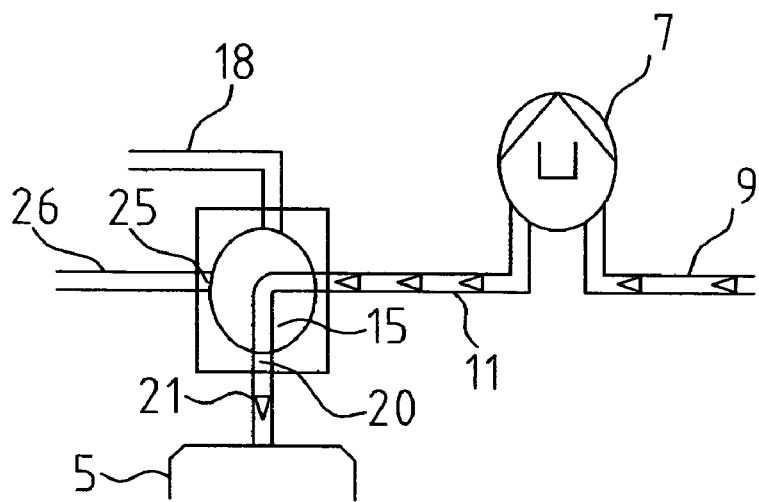
Figure 6C:
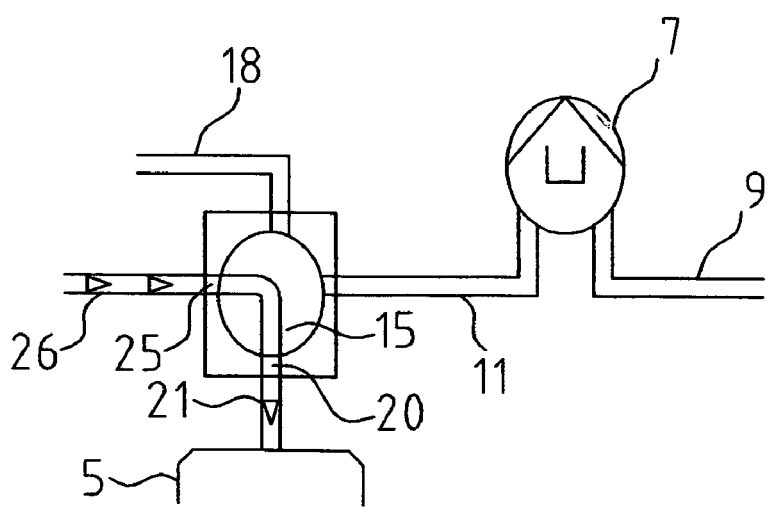

The sampling valve 12 has an internal flow controller 15 which controls flow of liquid through the sampling valve 12. Operation of this flow controller 15 is shown schematically in FIG. 6. In FIG. 6(a) the flow controller 15 is shown connecting the first sample inlet 14 with a bypass outlet 16. The bypass 16 connects to a bypass line 18. In this configuration a liquid sample is delivered by the sample pump 7 to the bypass line 18. FIG. 6(b) shows the flow controller 15 rotated through 90° to connect the first sample inlet 14 with a sample valve reactor outlet 20 which communicates through a transfer pipe 21 with a sample inlet 22 of the reactor vessel 5. In this configuration a liquid sample is delivered by the sample pump 7 to the reactor vessel 5. FIG. 6(c) shows the flow controller 15 rotated through a further 90° to connect the outlet 20 with a base inlet 25. The base inlet 25 connects to a base inlet line 26 leading from an outlet 27 of a base pump 28. An inlet 29 of the base pump 28 connects via an inlet line 30 to a base reservoir 31.

The reactor vessel 5 has an outlet 35. A circulation pump 36 is mounted in a pipe 37 connected between the outlet 35 and a recirculation inlet 38 of the reactor vessel 5.

The ozone generator 6 has an outlet line 41 leading to ozone inlet 42 of the reactor vessel 5. An ozone outlet pipe 43 leads from the reactor vessel 5 through an ozone destructor 44 and exhaust valve 46 to exhaust.

An acid pump 47 has an inlet 48 and outlet 49. The inlet 48 connects through inlet pipe 50 with an acid reservoir 51. The outlet 49 connects through acid delivery line 52 with the reactor vessel 5.

The reactor vessel outlet 35 also connects through a discharge line 55 with an inlet pipe 56 of a sample chamber 57. A stop valve 57 is mounted in the discharge line 55. An analysis pump 58 has an inlet 59 and outlet 60. The inlet 59 connects through a suction line 61 with the sample chamber 57. The outlet 60 of the analysis pump 58 connects through a delivery line 64 with a detector 66. The detector 66 has a light source 67 for directing light through a translucent measurement cell 68 located in the delivery line 64. Light transmitted by the light source 67 through the measurement cell 68 is sensed by a detector 69 located at an opposite side of the measurement cell 68. Downstream of the measurement cell 68 the delivery line 64 leads to a drain 72.

A cleaning pump 85 has an inlet 86 connected by cleaning fluid suction pipe 87 to a cleaning fluid reservoir 88. An outlet 89 of the cleaning pump 85 connects through a cleaning fluid supply line 90 and a cleaning fluid 3-way valve 91 with the delivery line 64.

A flushing pump 95 has an inlet 96 connected by a water suction pipe 97 to a water supply 98. An outlet 99 of the water pump 95 connects through water delivery line 100 with a flushing valve 101 in the delivery line 64.

In operation, the sample pump 7 is operated to deliver a liquid sample through the sampling valve 12 and out through the bypass line 18. The flow controller 15 is in the position shown in FIG. 6(a).

When a fresh liquid sample is at the sampling valve 12 the flow controller 15 rotates clockwise by 90° to the position shown in FIG. 6(b) and a measured quantity of the liquid sample is pumped into the reactor vessel 5 by the sample pump 7. Typical sample volumes are up to 10 ml and may be reduced in steps to 0.4 ml depending on the range to be measured.

The flow controller 15 of the sampling valve 12 is rotated clockwise by a further 90° into the position shown in FIG. 6(c). In this position the sample remaining in the transfer pipe 21 is flushed by base delivered from the base pump 28 through the sampling valve 12. This also raises the pH in the reactor vessel 5 to greater than pH 12 and preferably about pH 14.

The circulation pump 36 is operated, the ozone generator 6 is switched on and the oxygen flow control device 45 gives a measured flow of oxygen gas through the ozone generator 6 and into the reactor vessel 5. The sample is oxidised in the reactor vessel 5 using hydroxyl radicals.

At the same time, the flow controller 15 in the sampling valve 12 is reversed through 180° returning to its start position which is shown in FIG. 6(a). The sample pump 7 is run in reverse, emptying the sample line 11. Conveniently at the same time, the spent fluid from a previous reaction was collected in a container as it was discharged through the drain outlet 23, a cleaning valve 110 mounted in the bypass line 18 can be activated while the sample pump 7 is running in reverse, and this acidic material is then used to wash the sample line 11 and keep it clean, without the use of additional chemicals. This can be seen more clearly in FIG. 5.

When oxidation is complete, the acid pump 47 is operated and the pH in the reactor vessel 5 is reduced to below pH 1. Any carbon dioxide in the liquid is sparged off by the flow of oxygen.

The acid also contains a small amount of catalyst, for example manganese. This is used as a catalyst in the reaction, and it is desirable as it converts oxalate to carbon dioxide gas. The purpose of the catalyst is to eliminate interference from oxalate (it also supports 100% recovery of all carbon). By using a combination of acids with and without catalyst this technique can be extended to Include measurement of oxalates in the sample.

When all the carbon dioxide has been released, the stop valve 57 downstream of the reactor vessel outlet 35 opens, the exhaust valve 46 closes and the liquid in the reactor vessel 5 is dumped to the sample chamber 57. A drain valve 62 of the sample chamber 57 is closed so that the liquid remains trapped in the sample chamber 57.

At this point nitrogen analysis of the liquid in the sample chamber 57 starts.

However, in order to save time, the oxidation process as described previously repeats to prepare a new sample liquid for testing. Prior to reception of the sample liquid in the sample chamber 57 the measurement portion 3 will be made ready for analysis by filling the measuring cell 68 with clean water, delivered through the delivery line 64 by the water pump 95, and a blank spectrum is obtained for the clean water sample.

The analysis pump 58 is run until the measuring cell 68 is full of oxidised sample delivered from the sample chamber 57 by the analysis pump 58. The light source 67 switches on. The light source 67 can conveniently be provided by a deuterium lamp, which gives a good spectral output from below 200 nm to above 400 nm. Other light sources may be used for measurement in different spectral areas. The spectrum is measured using the detector 69 which has a photodiode array. The primary measuring frequency is 217 nm, and other frequencies can be used for comparison. This spectrum is compared with the blank spectrum obtained for the clean water as mentioned above and the measurement is calculated to give a measurement of total nitrogen content in the sample.

The nitrogen measuring system is then cleaned. The analysis pump 58 runs in reverse, emptying the delivery line 64. The drain valve 62 opens, a purge valve 63 changes state so that a flow of oxygen gas from the flow controller 45 forces the liquid in the sample chamber 57 through the drain valve 62 and out to drain 23.

The cleaning valve 91 changes state, and the cleaning pump 85 is run for about two seconds flushing the measuring cell 68 with a cleaning fluid. A typical cleaning solution will be HCl in water approximately 1.8N. This cleaning fluid remains in the measurement cell 68 for about one minute. The cleaning pump 85 is then run for two seconds and then in reverse for two seconds. This has the effect of pushing the contaminated cleaning fluid down the drain 72 and at the same time recovering the cleaning fluid used to flush the contaminated cleaning fluid from the measuring cell 68. When the cleaning pump 85 has run in reverse for approximately two seconds then the measurement cell 68 and lines from the cleaning valve 91 to the drain should be empty.

The flushing valve 101 is then opened and the water pump 95 is run for about twenty seconds filling flushing water through the delivery line 64 washing any traces of cleaning fluid from the measurement cell 68 and filling the measurement cell 68 with clean water ready for measuring the blank spectrum as described previously. This process described above is then repeated at timed intervals as required.

Figure 2:
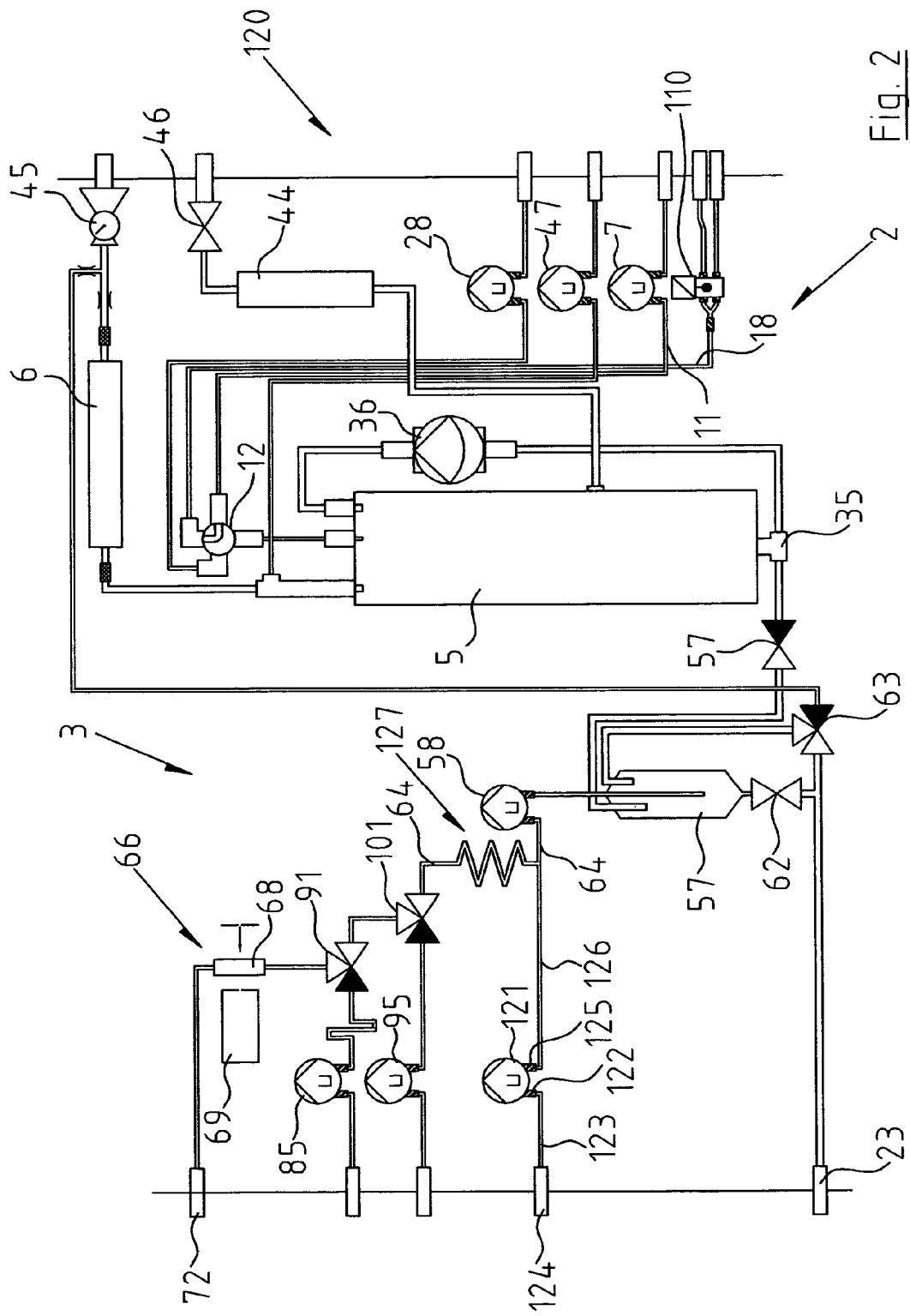
FIG. 2 is a schematic illustration of another analyser according to a second embodiment of the invention.

Referring now to FIG. 2 there is shown another liquid analyser according to a second embodiment of the invention indicated generally by the reference numeral 120. This is largely similar to the liquid analyser described previously with reference to FIG. 1 and like parts are assigned the same reference numerals. The measurement portion 3 of the liquid analyser 120 in this case further includes a reagent pump 121 having an inlet 122 connected by a suction pipe 123 with a reagent reservoir 124. An outlet 125 of the reagent pipe 121 discharges through pipe 126 into the delivery line 64. A mixer 127 which optionally includes a heater or a hydrolysing unit is provided in the delivery line 64 for mixing reagent with the sample liquid discharged from the analysis pump 58 prior to delivery of the mixture to detector 66.

In operation, the liquid sample is prepared in the reactor and delivered to the sample chamber 57 in the same way as was described previously for the liquid analyser of FIG. 1. For nitrogen analysis the analysis pump 58 runs and after a short delay of about three seconds the reagent pump 121 runs. The fluids discharged from the pumps 58, 121 mix in the mixture tube 127. When mixed, the mixture is pumped into the measuring cell 68 and measured, typically at a single wavelength. Both nitrogen and phosphate can be measured at 400 nm. The measurement is calculated from this reading and the blank spectrum. The measurement portion 3 is cleaned in the same way as described previously for the liquid analyser of FIG. 1. The process is repeated at timed intervals.

Figure 3:
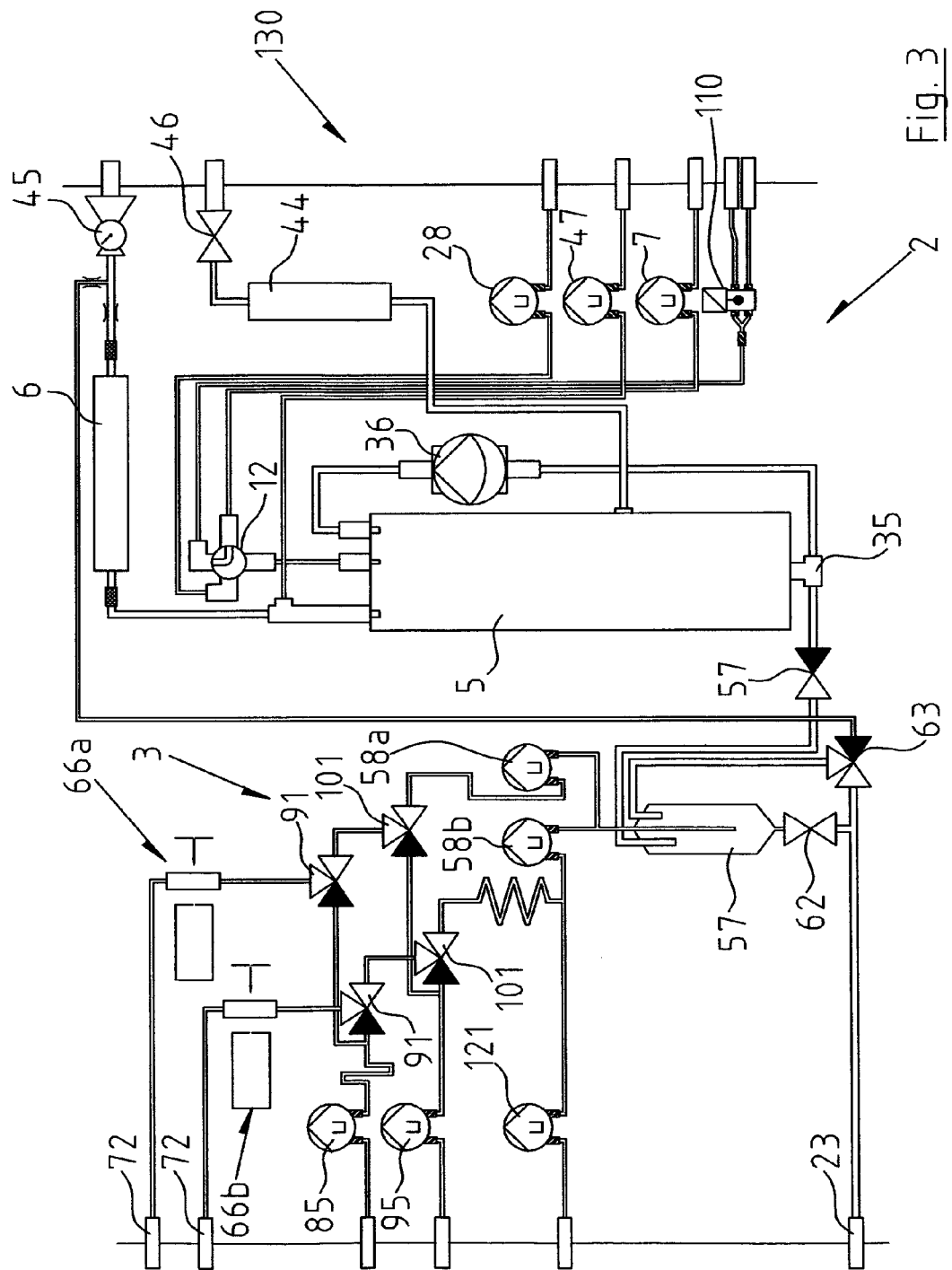
FIG. 3 is a schematic illustration of another analyser according to a third embodiment of the invention.

Referring to FIG. 3 there is shown another liquid analyser according to a third embodiment of the invention indicated generally by the reference numeral 130. This liquid analyser 130 is largely similar to the liquid analyser described previously and like parts are assigned to the same reference numerals. In this case, the measurement portions 3 of the analysers shown in FIGS. 1 and 2 have essentially been combined and the operation is largely similar. However, a separate nitrogen analyser pump 58(*a*) and a phosphate analyser pump 58(*b*) are provided for delivery of liquid from the sample chamber 57 through separate nitrogen detector 66(*a*) and phosphate detector 66(*b*) respectively.

Figure 4:
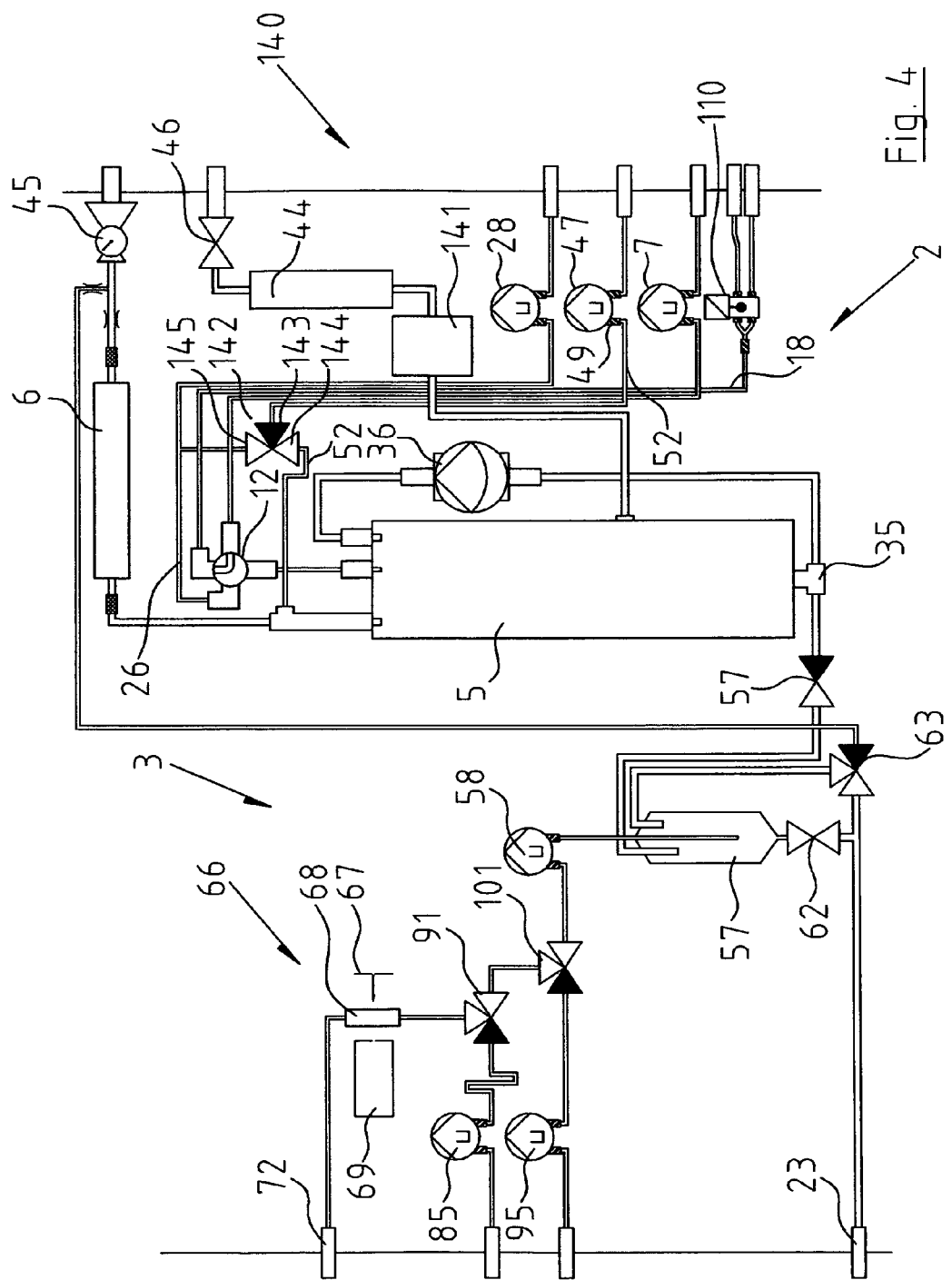
FIG. 4 is a schematic illustration of another analyser according to a fourth embodiment of the invention.

FIG. 4 shows another liquid analyser according to a fourth embodiment of the invention indicated generally by the reference numeral 140. Parts similar to those described previously are assigned the same reference numerals. This is essentially the same as the liquid analyser shown in FIG. 1 except that In this case a carbon dioxide analyser 141 is mounted in the outlet pipe 43 between the reactor vessel 5 and the ozone destructor 44. Analysers, such as infra red analysers for example, for other materials could be inserted here also. The carbon dioxide analyser 141 measures the carbon dioxide gas released from the oxidised solution in the reactor vessel 5 when the pH is reduced to one. With an appropriate calibration the gas measurement can be converted to total carbon, or total organic carbon if the total inorganic carbon is known. The carbon dioxide analyser 141 or other analyser could similarly be inserted in any of the liquid analysers shown in FIGS. 2, 3 and 5 if desired.

In this case also a 3-way acid control valve 142 is provided in the acid delivery line 52. This valve 142 has an inlet 143 connected to the outlet 49 of the acid pump 47, a first valve outlet 144 connected to the reactor vessel 5 and a second valve outlet 145 which connects to the base inlet line 26 for delivery of acid to the base inlet 25 the sampling valve 12. Normally the second outlet 145 will be shut and the first outlet 144 will be open. This configuration corresponds to the configuration shown in FIG. 1. The valve 142 can be switched to shut the first outlet 144 and open the second outlet 145. This allows acid to be delivered to the reactor vessel 5 with the liquid sample initially to lower the pH. Carbon dioxide formed can be stripped off to measure total inorganic carbon present in the sample prior to switching back the valve 142 and adding the base to the reactor vessel 5.

Figure 5:
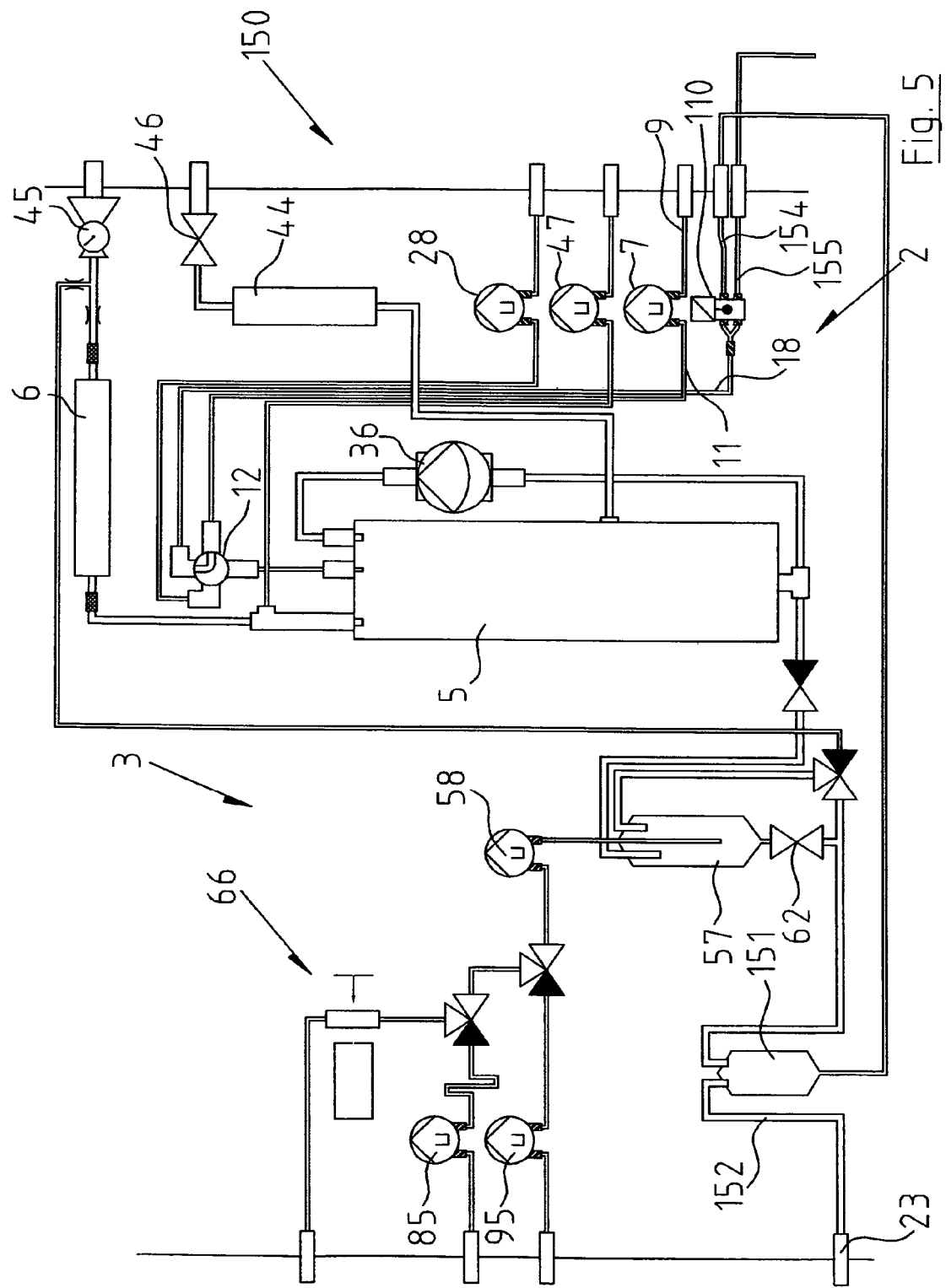
FIG. 5 is a schematic illustration of another analyser according to a fifth embodiment of the invention.

Referring now to FIG. 5 there is shown another liquid analyser according to a fifth embodiment of the invention indicated generally by the reference numeral 150. Parts similar to those described previously are assigned the same reference numerals. This is largely similar to the liquid analyser shown in FIG. 1 however in this case provision is provided for cleaning the sample delivery line 11 by collecting the spent chemicals for the reactor vessel 5. These are collected in a vessel 151 which has a safety overflow 152 to the drain 23. When the sample pump 7 runs in reverse and the cleaning valve 110 is switched so that the upper line 154 is open and the lower bypass drain line 155 is closed the spent chemicals are brought from the vessel 151 and drawn through the sample valve 12 and into the sample line 11 and through the sample pump 7 and out through the inlet line 9 to clean the sample loop.

Figure 7A:
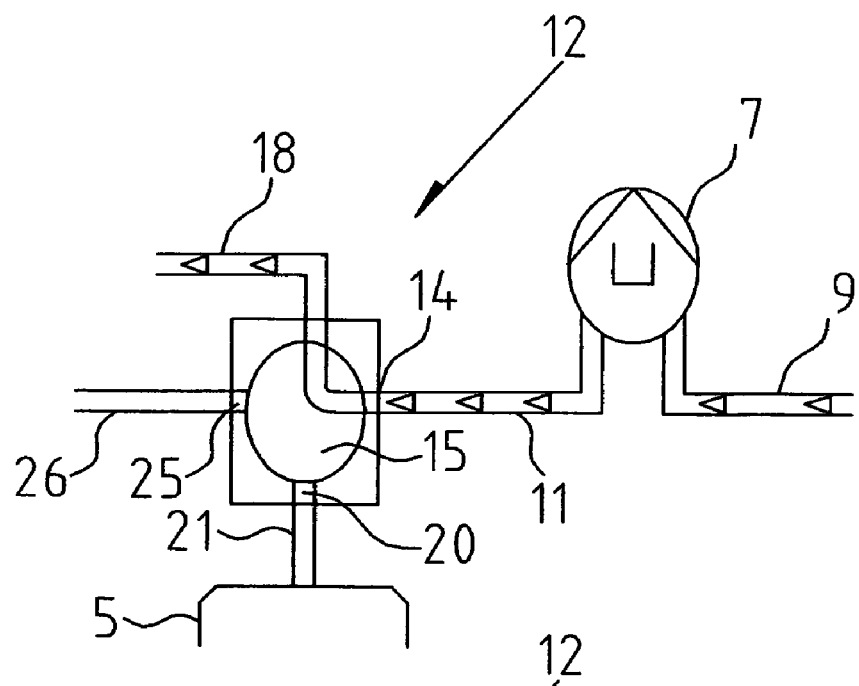
FIG. 7 has schematic views similar to FIG. 6 showing the sampling valve in another mode of operation.
Figure 7B:
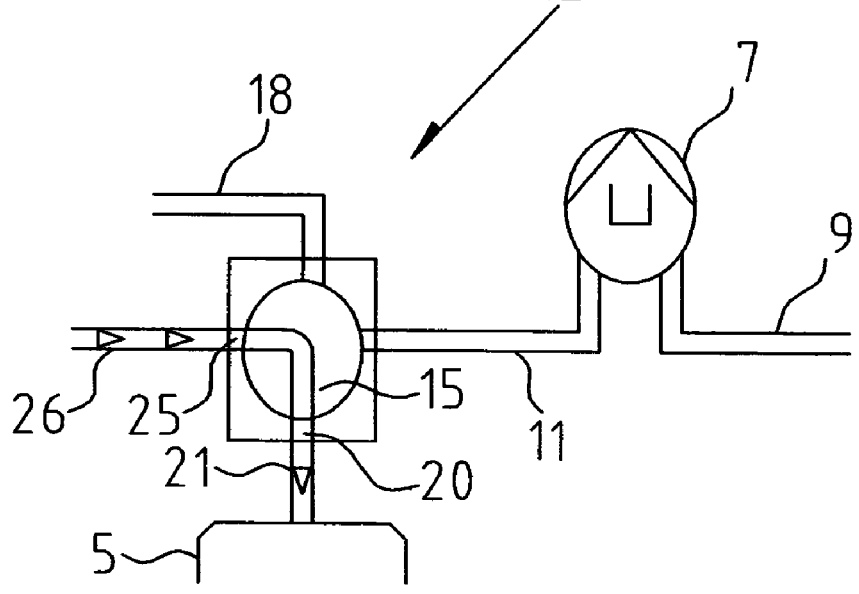

FIG. 7 shows operation of the valve 12 for very small samples. In FIG. 7(*a*) the sample liquid is pumped y sample pump 7 through valve 12 to bypass line 18. The controller 15 is then turned through 180°, as shown in FIG. 7(*b*), and the sample used for analysis in the liquid container in the valve 12. The volume of this sample is 0.08 ml. The sample is flushed into the reactor vessel 5 by the base or acid where appropriate delivered through line 26. The controller 15 is then returned through 180° to the position shown in FIG. 7(*a*) for reception of the next sample.

The concentration of various materials in the oxidised solution can be measured either directly or by colorimetric methods such as those outlined below.

Total Phosphate Analysis

The Total Phosphorus is measured by Vanadomolybdophosphoric Acid Colorimetric Method (Standard Methods for the Examination of Water and Wastewater, $20^{th}$ Edition, 1998, APHA, AWWA,WEF. Method 4500-P B and C.). The principle of method is that in Phosphate containing solutions, Ammonium Molybdate reacts in an acid medium to form a Heteropoly Acid, Molybdophosphoric Acid. The reagent used in analysis is called Vanadate-Molybdate Reagent. In the presence of Vanadium the Vanadomolybdophosphoric Acid (yellow colour) is formed. The intensity of the yellow colour at 400 nm is proportional to the Phosphate concentration in the solution. Above techniques measure Total Reactive Phosphorus, Total Acid-Hydrolysable Phosphorus, Total Phosphorus (after oxidation with Ozone and Hydroxyl Radicals) and Total Organic Phosphorus.

Total Nitrogen Analysis

The Total Nitrogen in samples (oxidised with Ozone and Hydroxyl Radicals) is measured with UV Spectrophotometric Screening Method (Standard Methods for the Examination of Water and Wastewater, $20^{th}$ Edition, 1998, APHA, AWWA,WEF. Method 4500-$NO_3$ B.). The principle of this technique is the absorbance of UV light at 217-220 nm is proportional to the Nitrate concentration in the solution. The oxidation with Ozone and Hydroxyl Radicals allows measuring Total Nitrogen, which includes Ammonia Nitrogen, Organic Nitrogen and Nitrite.

The Total Nitrogen may also be measured by a Colorimetric Method. The reagent used in this method is an Acid Reagent. The principle of this technique is absorbance at 40 nm due to the yellow colour formation between Nitrate and Acid complex is proportional to the Nitrate concentration n the solution. After oxidation with Ozone and Hydroxyl Radicals, this technique can measure Total Nitrogen including Ammonia Nitrogen, Organic Nitrogen and Nitrite.

Total Copper Analysis

The Total Copper is measured by Bathocuproine Method (Standard Methods for the Examination of Water and Wastewater, $20^{th}$ Edition, 1998, APHA, AWWA,WEF. Method 3500-Cu C.). The principle of method is that Cuprous ion forms a water-soluble orange coloured chelate with Bathocuproine Disulfonate reagent. The absorbance of the colour at 484 nm is proportional to the copper concentration in the solution. After oxidation with ozone and hydroxyl radicals, all liquid samples containing copper compounds can be analysed with this method.

Total Aluminium Analysis

The Total Aluminium is measured by Erichrome Cyanine R Method (Standard Methods for the Examination of Water and Wastewater, $20^{th}$ Edition, 1998, APHA, AWWA,WEF. Method 3500-Al B.). The principle of method is that with Erichrome Cyanine R dye, Aluminium solutions forms a red to pink complex, which exhibits maximum absorption at 535 nm. The intensity of the developed colour is proportional to the Aluminium concentration in solution. After oxidation with Ozone and Hydroxyl Radicals, all liquid samples containing Aluminium compounds can be analysed with this technique.

By applying similar standard measuring techniques other materials such as Cobalt, Manganese, Nickel etc. can also be analysed in the oxidised solution using the methods and apparatus of the invention.

It will be appreciated that the measurement portion of the analyser can be adapted as shown in FIG. 1 to provide a direct measurement of e.g. nitrogen in the sample using a photodiode array in the detector. Alternatively the measurement portion may be adapted for the addition of a colouring reagent, as shown in FIG. 2, prior to analysis and detection of a single characteristic wavelength. Different reagents can be provided for association with different flecked materials the analyser is requested to measure.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described, but may be varied in both construction and detail within the scope of the appended claims.

The invention claimed is:

1. A liquid analyser, including:
a reactor vessel;
an ozone generator having an ozone outlet connected to the reactor vessel to deliver ozone to the reactor vessel;
a sample pump having an inlet for connection to a source of a liquid to be tested, and an outlet connected to the reactor vessel through a sample delivery line;
a base solution reservoir;
a base pump having an inlet connected to the base solution reservoir and an outlet connected to the reactor vessel;
the reactor vessel having an outlet for discharge of oxidised liquid sample from the reactor vessel;
a multicomponent detector for determining multiple components in an oxidized liquid sample;
the multicomponent detector comprising at least one measuring cell for receiving the oxidised liquid sample, measuring the oxidised liquid sample optically using a frequency of absorption of at least one component in the oxidised liquid sample;
means for delivering the oxidised liquid sample to the multicomponent detector comprising: a sample chamber connected to the outlet of the reactor vessel for reception of oxidised liquid sample from the reactor vessel; and an analysis pump having an inlet connected to the sample chamber and an outlet connected to the multicomponent detector;
means for mixing a reagent with the oxidised liquid sample upstream of the multicomponent detector comprising: a mixer with an inlet and an outlet; and a reagent pump having an inlet connected to a reagent reservoir and an outlet connected to the inlet of the mixer, the outlet of the analysis pump also being connected to the inlet of the mixer, the outlet of the mixer being connected to the multicomponent detector; and
wherein the analysis pump is reversible for flowing oxidised liquid sample into a sample chamber upstream of the measuring cell after a measurement has been made.

2. The analyser as claimed in claim 1 wherein means is provided for delivering a cleaning fluid to the detector for cleaning the detector and means is provided for delivering a flushing fluid to the detector.

3. The analyser as claimed in claim 1 wherein the multicomponent detector is an optical detector.

4. The analyser as claimed in claim 1 wherein an acid pump is provided having an inlet for connection to an acid reservoir and an outlet connected to the reactor vessel.

5. The analyser as claimed in claim 1 wherein means is provided for cleaning a sample delivery line communicating between the sample pump and the reactor vessel.

* * * * *